United States Patent
Gao et al.

(10) Patent No.: US 11,852,576 B2
(45) Date of Patent: Dec. 26, 2023

(54) METHOD FOR DETERMINING THE PORE SIZE DISTRIBUTION IN A RESERVOIR

(71) Applicant: SAUDI ARABIAN OIL COMPANY, Dhahran (SA)

(72) Inventors: Jun Gao, Dhahran (SA); Marwah Mufid AlSinan, Al Qatif (SA); Hyung Tae Kwak, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/649,473

(22) Filed: Jan. 31, 2022

(65) Prior Publication Data
US 2023/0243728 A1    Aug. 3, 2023

(51) Int. Cl.
G01N 15/08    (2006.01)
G01N 33/24    (2006.01)
E21B 49/02    (2006.01)
G01N 24/08    (2006.01)
G01V 3/32    (2006.01)

(52) U.S. Cl.
CPC .......... *G01N 15/088* (2013.01); *E21B 49/02* (2013.01); *G01N 15/08* (2013.01); *G01N 24/081* (2013.01); *G01N 33/24* (2013.01); *G01V 3/32* (2013.01)

(58) Field of Classification Search
CPC .... G01N 15/088; G01N 15/08; G01N 24/081; G01N 33/24; E21B 49/02; G01V 3/32
See application file for complete search history.

(56) References Cited

U.S. PATENT DOCUMENTS 10,324,222 B2 *  6/2019  Chen ...................... E21B 49/02
10,697,295 B2 *  6/2020  Buono ..................... G01V 3/14
(Continued)

FOREIGN PATENT DOCUMENTS

WO    2018/164953 A1    9/2018
WO    2019/232299 A1    12/2019

OTHER PUBLICATIONS

Blunt, Martin J. et al., "Pore-scale imaging and modelling"; Advances in Water Resources, vol. 51; pp. 197-216; Jan. 2013 (20 pages).
(Continued)

*Primary Examiner* — Ryan D Walsh
(74) *Attorney, Agent, or Firm* — Osha Bergman Watanabe & Burton LLP

(57) ABSTRACT

A method for determining the pore size distribution in a reservoir, including the steps: drilling a core sample out of the reservoir, determining a porosity distribution along the core sample, obtaining $T_2$-distributions at different saturation levels of the core sample with formation brine, performing time domain subtraction on the $T_2$-distributions to obtain $T_2$-distributions at all saturation levels, determining the pore throat size distribution along the core sample, determining first porosities from the $T_2$-distributions that correspond to second porosities of the pore throat size distribution for each saturation level, determining $T_2$-distributions at the first porosities from the $T_2$-distributions, determining pore throat sizes at the second porosities from the pore throat size distributions, plotting the pore throat sizes as function of the relaxation times $T_2$ to obtain the surface relaxation, and determining the pore size distribution of the reservoir.

10 Claims, 12 Drawing Sheets

(56) References Cited

U.S. PATENT DOCUMENTS

| | | | |
|---|---|---|---|
| 10,948,439 B2* | 3/2021 | AlSinan | G01R 33/44 |
| 10,969,353 B2* | 4/2021 | Kwak | G01N 24/081 |
| 11,287,546 B2* | 3/2022 | Alharbi | G01V 3/38 |
| 11,391,683 B2* | 7/2022 | Gao | G01N 33/24 |
| 11,573,348 B1* | 2/2023 | Gao | G01V 3/38 |
| 2016/0139291 A1 | 5/2016 | Saidian et al. | |
| 2023/0152253 A1* | 5/2023 | AlSinan | G01N 33/24 |
| | | | 324/309 |

OTHER PUBLICATIONS

Chen, Q. et al., "A Single-Shot Method for Capillary Pressure Curve Measurement Using Centrifuge and Quantitative Magnetic Resonance Imaging"; Proceedings of the 2006 SPE/DOE Symposium on Improved Oil Recovery; Paper No. SPE-100059-MS; pp. 1-8; Apr. 22, 2006 (8 pages).

Marschall, D. et al., "Method for Correlating Nmr Relaxometry and Mercury Injection Data"; Proceedings of the 1995 SCA Conference; Paper No. 9511; pp. 1-12; 1995 (12 pages).

Vashaee, S. et al., "Region of interest selection of long core plug samples by magnetic resonance imaging: profiling and local T2 measurement"; Measurement Science and Technology; vol. 25, No. 3, Article 035004; pp. 1-10; Feb. 5, 2014 (10 pages).

Zhang, Pengfei et al., Petrophysical characterization of oil-bearing shales by low-field nuclear magnetic resonance (NMR); Marine and Petroleum Geology; vol. 89, Part 3; pp. 775-785; Jan. 2018 (40 pages).

\* cited by examiner

METHOD FOR DETERMINING THE PORE SIZE DISTRIBUTION IN A RESERVOIR

BACKGROUND

Sedimentary rocks are formed by the accumulation or deposition of minerals or organic particles followed by cementation. Sediments are particles of the sedimentary rock. Porosity is the percentage of pore volume within a rock that contains fluids like oil, gas, or water. The fluids are accumulated during the geological time.

Once a well is drilled in a reservoir, the fluids flow to the well for oil recovery. The pore volume starts as the space between distant solid particles and undergoes various depositional and diagenetic processes that changes the sediments physically and chemically. The changes might become extremely complex, especially for sedimentary rocks comprising carbonate minerals (carbonate rocks).

Irregular microscopic pore volumes can only be accurately and fully geometrically described by a virtual 3D model, recreated by X-rays that create cross-sections of the rock (X-ray microtomography).

Some common concepts or properties of the porous reservoir rock are derived by the microscopic pore volume. For example, the pore volume is a quantification of the total volume. Other properties are based on assumptions or simplification of the microscopic pore volume. One property is the distribution of the pore sizes, which depends on the measurement methods and assumptions. Even the individual pores are not be easily defined for some complex pore volume.

Accordingly, there exists a need for a method for determining the pore size distribution in a reservoir.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments disclosed herein relate to a method for determining the pore size distribution in a reservoir, comprising the steps: drilling a core sample out of the reservoir, determining a porosity distribution along the core sample, obtaining $T_2$-distributions at different saturation levels of the core sample with formation brine, performing time domain subtraction on the $T_2$-distributions to obtain $T_2$-distributions at all saturation levels, determining the pore throat size distribution along the core sample, determining first porosities from the $T_2$-distributions that correspond to second porosities of the pore throat size distribution for each saturation level, determining $T_2$-distributions at the first porosities from the $T_2$-distributions, determining pore throat sizes at the second porosities from the pore throat size distributions, plotting the pore throat sizes as function of the relaxation times $T_2$ to obtain the surface relaxation, and determining the pore size distribution of the reservoir.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
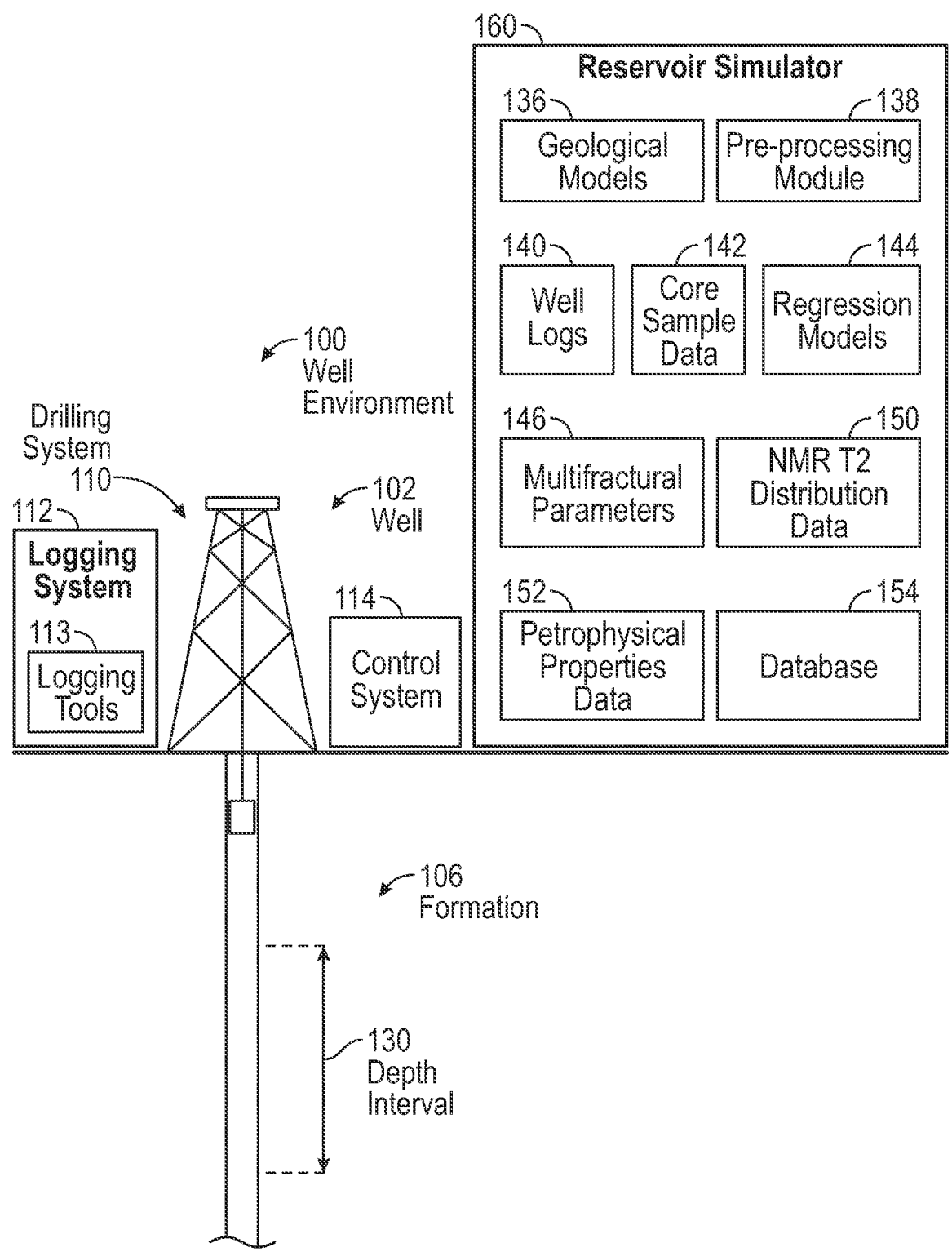
FIG. 1 illustrates a well environment in accordance with one or more embodiments disclosed herein.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments disclosed herein determine surface relaxivity by Nuclear magnetic resonance (NMR) measurements. The surface relaxivity is the key parameter that relates the relaxation time to the pore radius. NMR relaxometry typically involves the analysis of a relaxation time distribution. NMR measurement is non-destructive and is conveniently integrated into existing laboratory procedures. However, the surface relaxivity cannot be easily determined. Previous calibration methods usually involve different physical principles or give effective relaxivity including other properties.

In one aspect, embodiments disclosed herein relate to a method for determining the pore size distribution in a reservoir. The method involves drilling a core sample out of the reservoir, determining a porosity distribution along the core sample, obtaining saturation profiles, $T_2$-distributions at different saturation levels of the core sample with formation brine, performing time domain subtraction on the $T_2$-distributions to obtain $T_2$-distributions at all saturation levels, determining the pore throat size distribution along the core sample, determining first porosities from the $T_2$-distributions that correspond to second porosities of the pore throat size distribution for each saturation level, determining $T_2$-distributions at the first porosities from the $T_2$-distributions, determining pore throat sizes at the second porosities from the pore throat size distributions, plotting the pore throat sizes as function of the relaxation times $T_2$ to obtain the surface relaxation, and determining the pore size distribution of the reservoir.

The pore throat is the microscopic pore space at the point where two grains meet. The point connects two larger pore volumes. The number, size, and distribution of the pore throats control the resistivity, flow and capillary-pressure characteristics of the rock.

The method for obtaining the intrinsic relaxation time takes advantage of multiple NMR measurements and conducts comprehensive data analysis to obtain the relaxation time. The combined analysis of the $T_2$-distributions and pore throat size of all saturation levels gives the relaxation by linear regression.

FIG. 1 illustrates a well environment 100 that comprises a well 102 having a wellbore 104 extending into a formation 106. The wellbore 104 comprises a bored hole that extends from the surface into a target zone of the formation 106, such as a reservoir. The formation 106 comprises various formation characteristics of interest, such as formation porosity, formation permeability, water saturation, irreducible water saturation, rock type, temperature, and density. The porosity indicates how much space exists in a particular rock within an area of interest in the formation 106, where oil, gas, and/or water is trapped. The permeability indicates the ability of liquids and gases to flow through the rock within the area of interest. Water saturation indicates the fraction of water in a given pore space. Irreducible water saturation indicates the ratio of irreducible total fluid volume to effective porosity for a formation 106 within the area of interest. The rock type indicates the type of rock for a formation 106 with the area of interest. For example, a tight chalk has a high strength property that requires a high pump pressure for breaking the chalk. The temperature indicates the temperature or the temperature gradient for a formation 106 with the area of interest. The density indicates the bulk density for a formation 106 with the area of interest.

The well environment 100 comprises a drilling system 110, a logging system 112, a control system 114, and a reservoir simulator 160. The drilling system 110 comprises a drill string, a drill bit, a mud circulation system and/or the like for use in boring the wellbore 104 into the formation 106. The control system 114 comprises hardware and/or software for managing drilling operations and/or maintenance operations. For example, the control system 114 comprises one or more programmable logic controllers (PLCs) that include hardware and/or software with functionality to control one or more processes performed by the drilling system 110. Specifically, a PLC controls valve states, fluid levels, pipe pressures, warning alarms, drilling parameters (e.g., torque, WOB, SPP, RPM, etc.) and/or pressure releases throughout a drilling rig. In particular, a PLC is a ruggedized computer system with functionality to withstand vibrations, extreme temperatures, wet conditions, and/or dusty conditions, for example, around a drilling rig. Without loss of generality, the term "control system" refers to a drilling operation control system that is used to operate and control the equipment, a drilling data acquisition and monitoring system that is used to acquire drilling process and equipment data and to monitor the operation of the drilling process, or a drilling interpretation software system that is used to analyze and understand drilling events and progress.

The logging system 112 comprises one or more logging tools 113 (e.g., a NMR spectrometer) for use in generating well logs 140, core sample data 142 and NMR $T_2$ distribution data 150 of the formation 106. The logging tools 113 provide a powerful way to characterize the fine scale petrophysical properties data 152 (e.g., density, porosity, permeability, rock type, water saturation, irreducible water saturation, etc.).

Furthermore, as another example, the NMR logging tool measures the induced magnetic moment of hydrogen nuclei (e.g., protons) contained within the fluid-filled pore space of porous media (e.g., reservoir rocks). Thus, NMR logs measures the magnetic response of fluids present in the pore spaces of the reservoir rocks. In particular, NMR logs measures the magnetic response of fluids at the pore spaces of the reservoir rocks are fully saturated with water. Likewise, NMR logs measure the magnetic response of fluids at the pore spaces of the reservoir rocks only contain irreducible water after the fluid above a corresponding pore radius is removed from the reservoir rocks by adjusting a centrifugal force in a high-speed centrifuge. In so doing, NMR logs measure porosity (e.g., incremental porosity, cumulative porosity, total porosity, irreducible porosity, and movable porosity, etc.) and permeability, as well as the types of fluids present in the pore spaces. Thus, NMR logging is a subcategory of electromagnetic logging that responds to the presence of hydrogen protons rather than a rock matrix. Because hydrogen protons occur primarily in pore fluids, NMR logging directly or indirectly measure the volume, composition, viscosity, and distribution of pore fluids.

A logging tool 113 is lowered into the wellbore 104 and/or in the laboratory to acquire measurements (e.g., well logs 140), core sample data 142, and NMR $T_2$ distribution data 150 as the tool traverses a depth interval 130 (e.g., a targeted reservoir section) of the wellbore 104. The plot of the logging measurements versus depth is referred to as a "log" or "well log". Well logs 140 provides depth measurements of the well 102 that describe such reservoir characteristics as formation porosity, formation permeability, resistivity, density, water saturation, total organic content (TOC), volume of kerogen, Young's modulus, Poisson's ratio, and the like. The resulting logging measurements are stored and/or processed, for example, by the control system 114, to generate corresponding well logs 140 for the well 102. A well log comprises, for example, a plot of a logging response time versus true vertical depth (TVD) across the depth interval 130 of the wellbore 104.

Reservoir characteristics are determined using a variety of different techniques. For example, certain reservoir characteristics can be determined via coring (e.g., physical extraction of rock samples) to produce core samples and/or logging operations (e.g., wireline logging, logging-while-drilling (LWD) and measurement-while-drilling (MWD)). Coring operations comprises physically extracting a rock sample from a region of interest within the wellbore 104 for detailed laboratory analysis. For example, when drilling an oil or gas well, a coring bit cuts plugs (or "cores" or "core samples") from the formation 106 and bring the plugs to the surface, and these core samples are analyzed at the surface (e.g., in a lab) to determine various characteristics of the formation 106 at the location where the sample was obtained.

To determine porosity in the formation 106, various types of logging techniques are used. For example, the logging system 112 measures the water temperature in the formation 106 for characterizing water bearing zones and identifying vertical flow in the formation 106. This type of logging generates borehole temperature logs. Likewise, NMR logging measures NMR $T_2$ distribution to provide information about the fluid distribution, pore structure, and pore volume change to obtain important reservoir evaluation parameters (e.g., total porosity, effective porosity, permeability, irreducible saturation, and movable water saturation, etc.). In particular, NMR $T_2$ distribution comprises three components associated with bulk, surface, and diffusion (Equation 1). When the rock sample is fully water saturated, NMR $T_2$ distribution is dominated by the surface term $T_{2\_Surface}$. Thus, the NMR $T_2$ distribution is used to characterize pore size distribution of the rock sample (e.g., see the accompanying description to FIG. 2).

$$\frac{1}{T_2} = \frac{1}{T_{2\_Bulk}} + \frac{1}{T_{2\_Surface}} + \frac{1}{T_{2\_Diffusion}} \quad (1)$$

where $T_2$ is transverse relaxation time in ms of pore fluid, $T_{2\_Bulk}$ is bulk transverse relaxation time in ms of pore fluid, $T_{2\_Surface}$ is surface transverse relaxation time in ms of pore fluid, $T_{2\_Diffusion}$ is diffusion transverse relaxation time in ms of pore fluid.

Furthermore, NMR logging measures an NMR $T_{2c}$ value which is the $T_2$ boundary value between the movable fluid and the irreducible fluid. In particular, different types of rock affect the transverse relaxation time characteristics of NMR logging. Thus, the NMR $T_2$ value and the NMR $T_{2c}$ value is used to distinguish the rock type and other petrophysical properties for a formation of interest. For example, carbonate pores usually have an NMR $T_2$ distribution ranging from 0.01 to 1000 milliseconds (ms), and shale pores usually have an NMR $T_2$ distribution ranging from 0.01 to 10 ms. As another example, the medium-hand high-permeability sandstone reservoirs have an average NMR $T_{2c}$ value of 30.0 ms, and shale reservoirs have an average NMR $T_{2c}$ value of 8.3 ms.

Further, geosteering is used to position the drill bit or drill string of the drilling system 110 relative to a boundary between different subsurface layers (e.g., overlying, underlying, and lateral layers of a pay zone) during drilling operations. In particular, measuring rock properties during drilling provides the drilling system 110 with the ability to steer the drill bit in the direction of desired hydrocarbon concentrations. As such, a geosteering system uses various sensors located inside or adjacent to the drilling string to determine different rock formations within a well path. In some geosteering systems, drilling tools use resistivity or acoustic measurements to guide the drill bit during horizontal or lateral drilling.

Continuing with FIG. 1, the reservoir simulator 160 includes hardware and/or software with functionality to pre-process NMR $T_2$ distribution data 150 (e.g., a pre-processing module 138) to detect a rock sample which NMR $T_2$ distribution shows significant diffusion coupling based on the well logs 140. A diffusion coupling effect usually occurs in a rock sample in which fluids between pore throats 240 (see FIG. 2) with different radii are interconnected by diffusion. Thus, the diffusion coupling effect makes it difficult to distinguish the NMR $T_2$ distribution of meso pores and micro pores' throats in the same rock sample.

The pre-processing module 138 determines an NMR $T_{2c}$ value from NMR $T_2$ distribution data 150 for a targeted formation 106 of interest based on actual well logs 140. The determined NMR $T_{2c}$ value is saved in a database 154. For example, the NMR $T_{2c}$ value is used to determine free fluid index (FFI) and bulk volume of irreducible water saturation (BVI) for permeability and free fluid determination for the rock sample. For another example, the pre-processing module 138 applies a log-normal distribution (Equation 12) and a Gaussian fitting curve (Equation 2) to match meso pore NMR $T_2$ distribution data 150 to identify a diffusion coupling effect for the rock sample. In particular, the rock sample shows a significant diffusion coupling when meso and micro peaks of NMR $T_2$ distribution data 150 converge to the same peak.

$$f(t) = Ae^{-\frac{(t-\mu)^2}{2\sigma^2}} \quad (2)$$

where A is the amplitude, µ is the position, t is the time in the logarithmic scale, and a is the width.

In one or more embodiments, the reservoir simulator 160 includes hardware and/or software with functionality to determine one or more multifractal parameters (e.g., $D_{min}$ and $D_{max}$) based on the multifractal dimension analysis and the moment method. One important influencing factor of the rock properties is irregular microscopic pore spaces which follow a self-similarity rule. Thus, the rock pore structure is decomposed into intertwined fractal sets. Self-similarity means that a structure, or a process, and a part of it appear to be the same when compared. For example, fractals (e.g., patterns that form of smaller objects that look the same when magnified) is a well-known example of self-similarity and scale invariance. A self-similar system is associated with an underlying force that produce the self-similar system is the same at all scales, which results in the smaller parts and the larger parts looking like the whole. Thus, measurements of the methods of different resolving power show scaling properties of fractals based on the theory of fractals. A fractal structure is described by the basic-power law relationship (Equation 3) in which the frequency N of an occurrence of a given size δ is inversely proportional to a fractal dimension D of its size.

$$N = \frac{C}{\delta^D} \quad (3)$$

where D is the fractal dimension, N is the number of the elements, δ is length scale, and C is a constant.

Further, the reservoir simulator 160 determines one or more fractal dimensions $D_{NMR}$ (e.g., $D_{min}$ and $D_{max}$) based NMR $T_2$ distribution data 150, cumulative volume fraction of wetting fluid $V_c$, and maximum of resolvable relaxation time $T_{2max}$. In particular, for a capillary bundle tube model, if the minimum of resolvable relaxation time $T_{2min}$ is sufficiently small, there is a linear relationship between $\log V_c$ and $\log T_2$ (Equation 4). The fractal dimensions $D_{min}$ and $D_{max}$ is determined from a slope of the fitting curve of the double logarithmic presentation for the rock sample. For example, the fractal dimensions $D_{min}$ is associated with the largest slope of the fitting curve at a small NMR $T_2$ value for a small pore size. As another example, the fractal dimensions $D_{max}$ is associated with the smallest slope of the fitting curve at a large NMR $T_2$ value for a large pore size. Furthermore, the reservoir simulator 160 applies the moment method and a dyadic scaling-down to analyze multifractal spectrum $f(\alpha)$ of the probability function $p(\delta)$, mass exponents $\tau(q)$, singularity spectrum $\alpha(q)$, and generalized dimension $D(q)$ based on the pore size distribution on an interval (Equations 5, 6, 7, and 8).

$$\log(V_c) = (3 - D) \log(T_2) - (3 - D)\log T_{2max} \quad (4)$$

$$\tau(q) = -\lim_{\delta \to 0} \frac{\sum_{i=1}^{N(\delta)} p_i^q(\delta)}{\log \delta} \quad (5)$$

$$D(q) = \frac{\tau(q)}{1 - q} \quad (6)$$

$$a(q) = \frac{d\tau(q)}{dq} \quad (7)$$

$$f(a) = qa(q) - \tau(q) \quad (8)$$

where $V_c$ is cumulative volume fraction of wetting fluid, D is fractal dimension, $T_2$ is transverse relaxation time, $T_{2max}$ is the maximum of resolvable transverse relaxation time, q is the moment order, $\tau(q)$ is the mass exponents, $D(q)$ is generalized dimension, N is the number of the elements, $\delta$ is length scale, $p(\delta)$ is the probability function, $\alpha(q)$ is singularity spectrum, and $f(\alpha)$ is multifractal spectrum.

The reservoir simulator 160 also includes hardware and/or software with functionality to train and apply a regression model 144 (e.g., a linear regression model, a non-linear regression model) to predict NMR $T_{2c}$ based on multifractal parameters 146 (e.g., $D_{min}$ and $D_{max}$) and other petrophysical properties (e.g., FZI) determined using the multifractal dimension analysis for the rock sample of the formation 106. For example, the reservoir simulator 160 applies a linear regression model to determine a model to calculate NMR $T_{2c}$ based on multifractal parameters $D_{min}$ and $D_{max}$ (Equation 9) and other petrophysical properties (e.g., FZI) (Equations 10 and 11).

$$T_{2c\_room} = a(D_{min} - D_{max}) + b\left(\frac{D_{min}}{D_{max}}\right) + e \quad (9)$$

$$FZI = \left(\frac{1-\phi}{\phi}\right) \times \sqrt{\frac{k}{\phi}} \quad (10)$$

$$T_{2c\_room} = a(D_{min} - D_{max}) + b\left(\frac{D_{min}}{D_{max}}\right) + cFZI \quad (11)$$

where $T_{2c\_room}$ is NMR $T_{2c}$ measured for the fully water saturated rock sample at the room temperature, $D_{min}$ is minimal fractal dimension, $D_{max}$ is maximum fractal dimension, a, b, c, e are coefficients of the linear regression model, FZI is flow zone index, $\phi$ is porosity, and k is permeability.

In one or more embodiments, the reservoir simulator 160 applies a linear regression model 144 to determine a pore size based temperature correction of NMR $T_2$ distribution data 150 based on the temperature dependence of overall shape shift of NMR $T_2$ distribution (e.g., an NMR $T_2$lm mean difference) for the rock sample of the formation 106 (Equation 12). As the formation temperature is usually larger than the room temperature, the temperature dependence of NMR $T_2$ distribution varies depending on the reservoir rock sample. For example, the temperature dependence of NMR $T_2$ distribution is weak for some rock samples. As another example, the temperature dependence of NMR $T_2$ distribution shows a significant positive or negative correction for other rock samples. The temperature effect results from many factors (e.g., surface relaxation, bulk relaxation, fluids, and diffusion, pore size, etc.). For example, macro and micro pores show different degrees of temperature dependence of NMR $T_2$ distribution due to potential diffusion coupling and surface properties. In particular, the reservoir simulator 160 applies a Gaussian fitting curve (Equation 2) to determine the overall shape shift of NMR $T_2$ distribution of meso pores by comparing their NMR $T_2$lm mean difference at low and high temperatures. Likewise, the reservoir simulator 160 applies a log-normal distribution (Equation 12) to calculate NMR $T_2$lm mean difference as a function of temperature difference for meso pores of the rock sample.

$$\Delta T2lm(\%) = d \times (T - T_{room}) \quad (12)$$

where T is a temperature, $T_{room}$ is a room temperature, and d is a coefficient, and $\Delta T2lm$ is NMR $T_2$ logarithmic mean difference measured using a Gaussian fitting analysis between a temperature T and the room temperature $T_{room}$.

The reservoir simulator 160 also includes hardware and/or software with functionality to determine a temperature correct NMR $T_{2c}$ value using the temperature correction and the trained model based on multifractal parameters 146 (e.g., $D_{min}$, $D_{max}$), temperature, and other petrophysical properties (e.g., FZI) for the rock sample of the formation 106 (Equation 13). Likewise, the pre-processing module 138 determines petrophysical properties (e.g., permeability, irreducible saturation) using a free fluid model based on the Timur-Coates equation (Equation 14) for the rock sample of the formation 106.

$$T_{2c\_resevoir} = \quad (13)$$
$$(1 + d \times (T_{resevoir} - T_{room})) \times \left(a(D_{min} - D_{max}) + b\left(\frac{D_{min}}{D_{max}}\right) + cFZI\right)$$

$$k_{Coates} = \left[\left(\frac{\phi}{C}\right)^m \frac{FFI}{BVI}\right]^n \quad (14)$$

where $T_{2c\_resevoir}$ is NMR $T_{2c}$ at a formation temperature for the rock sample, $T_{resevoir}$ is the formation temperature, $T_{room}$ is the room temperature, $D_{min}$ is minimal fractal dimension, $D_{max}$ is maximum fractal dimension, a, b, c, d are coefficients of the linear regression model, FZI is flow zone index, $\phi$ is porosity, C, m, n are coefficients, BVI is bulk volume irreducible, and FFI is free fluid index.

Keeping with FIG. 1, a well path of a wellbore 104 is updated by the control system 114 using a geological model (e.g., one of the geological models 136). For example, a control system 114 communicates geosteering commands to the drilling system 110 based on well data updates that are further adjusted by the reservoir simulator 160 using a geological model 136. As such, the control system 114 generates one or more control signals for drilling equipment based on an updated well path design and/or a geological model. In some embodiments, the reservoir simulator 160 determines one or more formation top depths from seismic data and/or well log data. The reservoir simulator 160 uses these formation top depths to adjust the well path of the wellbore 104 accordingly.

While FIG. 1 shows various configurations of components, other configurations are used without departing from the scope of the disclosure. For example, various components in FIG. 1 are combined to create a single component. As another example, the functionality performed by a single component is performed by two or more components.

Figure 2:
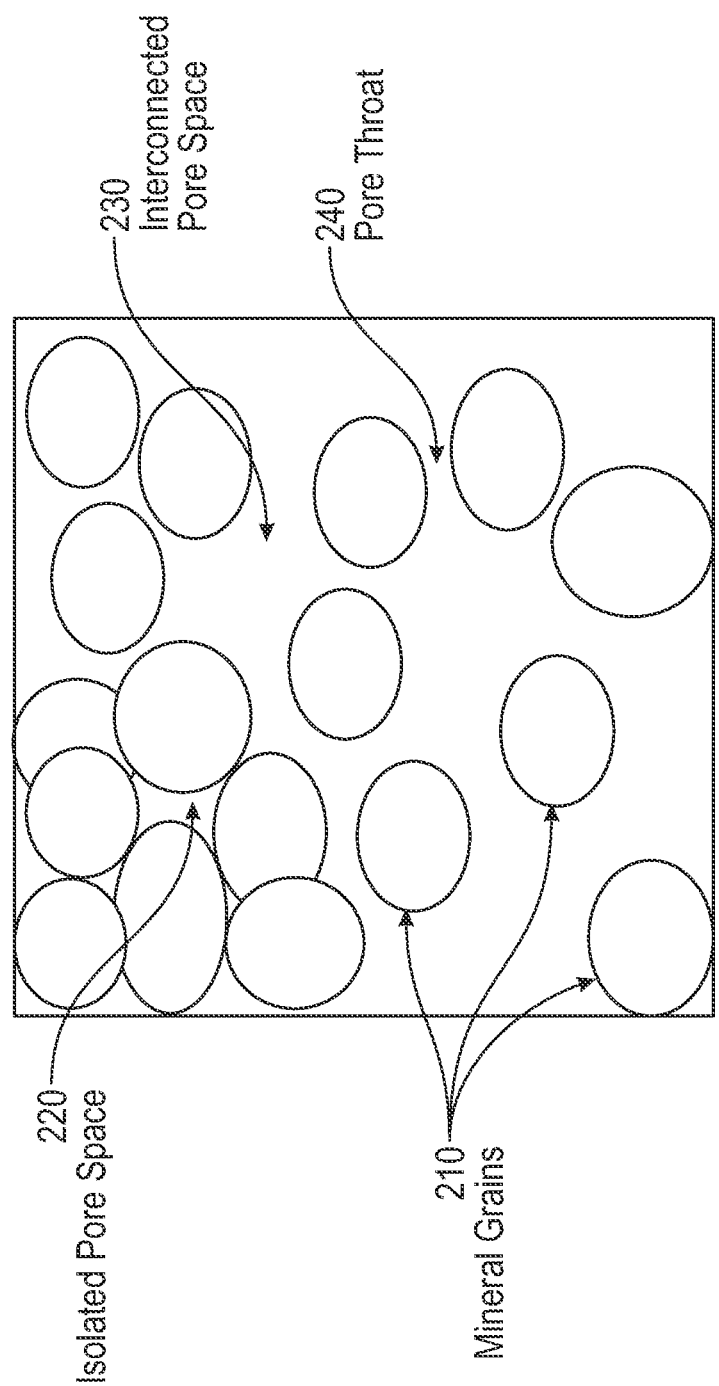
FIG. 2 shows an example of total porosity for a rock sample in accordance with one or more embodiments disclosed herein.

FIG. 2 shows an example of total porosity for a rock sample. Total porosity is associated with the total pore space which is the sum of isolated pore space 220 and interconnected pore space 230 in the rock bulk volume of mineral grains 210. In particular, isolated porosity is the percentage of isolated pore space 220 with respect to the bulk volume. Effective porosity is the percentage of interconnected pore space 230 with respect to the bulk volume. For example, determining effective porosity requires fluid flow to determine if pores are interconnected. At a given height above the free-water level, a capillary water becomes "irreducible". This capillary water and clay bound water (e.g., isolated porosity) forms the irreducible water saturation (Swi) with respect to effective porosity.

Figure 3:
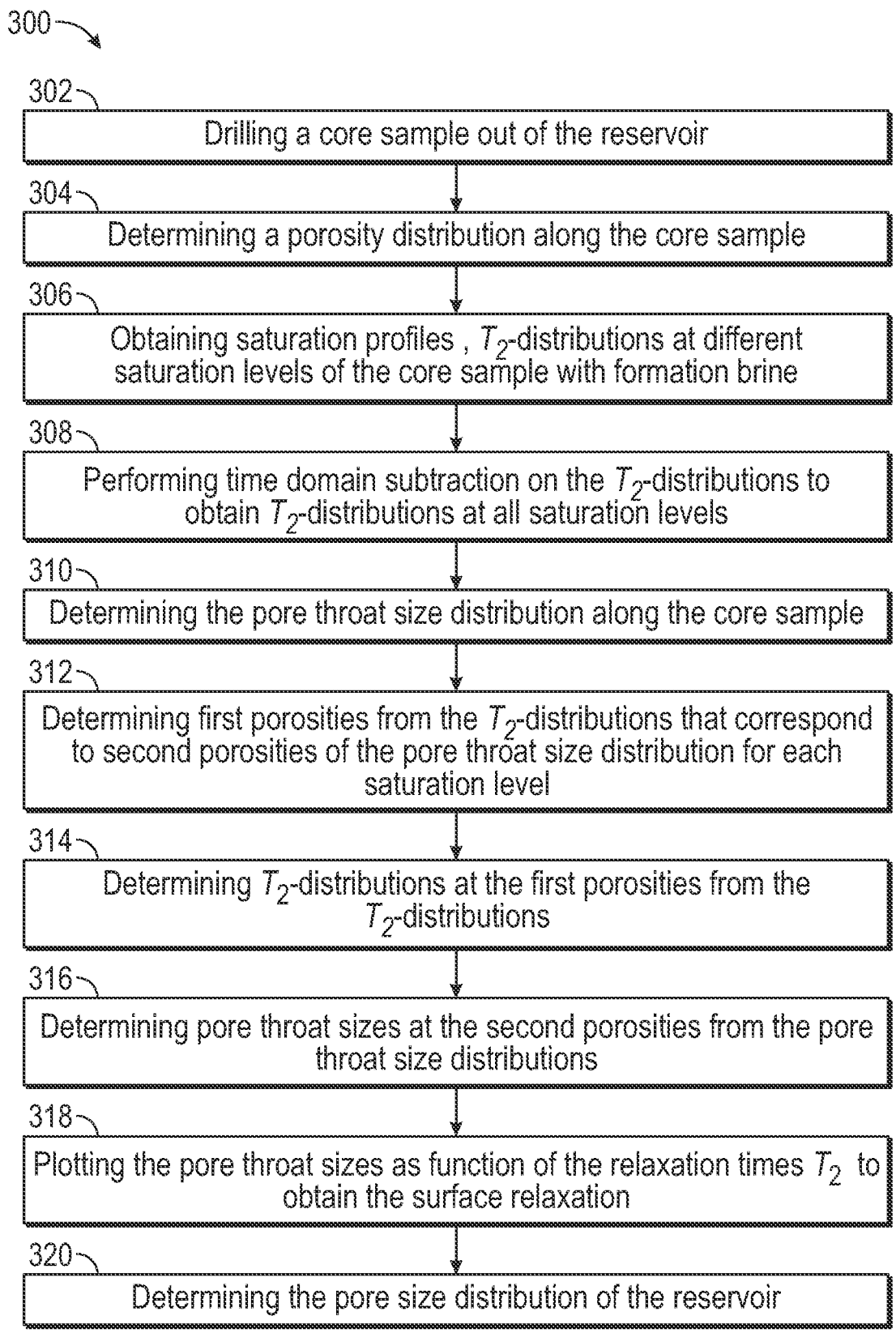
FIG. 3 shows a flowchart of the method steps for determining the pore size distribution in a reservoir in accordance with one or more embodiments disclosed herein.

FIG. 3 shows a flowchart 100 of the method steps for determining the pore size distribution in a reservoir, in accordance with one or more embodiments. One or more blocks of FIG. 3 are performed. While the various blocks in FIG. 3 are presented and described sequentially, one of ordinary skill in the art will appreciate that some or all of the blocks are executed in a different order, are combined or omitted, and some or all of the blocks are executed in parallel and/or iteratively. Furthermore, the blocks are performed actively or passively.

In step 302, a core sample is drilled out of the reservoir.

In step 304, a porosity distribution along the core sample is determined. The porosity distribution is determined by the measurement of the NMR profile along the core sample at full saturation of the core sample with water (Sw=100%).

In step 306, saturation profiles, $T_2$-distributions at different saturation levels of the core sample with formation brine, are obtained. The saturation profiles after each spin of the centrifuge are used to derive the capillary pressure along the core sample. The pore throat size distribution is calculated from the capillary pressure along the core sample.

In step 308, time domain subtraction on the $T_2$-distributions is performed to obtain $T_2$-distributions at all saturation levels.

The time domain subtraction is performed as follows. The difference between the different T2-distributions may be obtained by direct subtraction, with the caveat that this difference may have negative values. In case the subtraction is performed on the relaxation curves first (time domain), the T2-distribution after inversion results in positive values and is smooth. Thus, either method may be used for the subtraction without departing from the scope herein.

The $T_2$-distribution of saturation levels is obtained by time-domain subtraction of spatial or selective $T_2$ distribution measurements.

Regarding the spatial and selective $T_2$ distributions, the $T_2$-distribution of a fully water saturated core sample ($S_W$=100%) reflects the pore size distribution in the pore body. The saturation profile is uniform, if the core heterogeneity is negligible. However, since the centrifuge force varies with the distance from the centrifugal axis, the saturation varies with core length after spinning the core sample in a centrifuge. The end of the core sample near the axis has the lowest water saturation, while the far end has the highest saturation, with the capillary pressure of zero. When the $T_2$-distribution is performed on the partially-desaturated sample with a non-uniform saturation profile, the resulting pore size distribution represents the saturation along the core length. Three NMR methods are used to obtain the $T_2$-distribution at intermediate saturation levels: spatial $T_2$, selective $T_2$, and $T_2$ of uniform intermediate saturation levels.

In step 310, the pore throat size distribution is determined along the core sample. See Eq (2) below for the exact calculation of pore throat size distribution. The capillary pressure and pore throat size distribution are obtained by additional centrifuge speeds and spline fitting. The pore throat size is obtained through spline fitting from additional capillary pressure data points.

In step 312, first porosities from the $T_2$-distributions that correspond to second porosities of the pore throat size distribution are determined for each saturation level.

In step 314, $T_2$-distributions at the first porosities from the $T_2$-distributions are determined. An example of this step is given in the description of FIG. 10.

In step 316, pore throat sizes at the second porosities are determined from the pore throat size distributions. An example of this step is given in the description of FIG. 10.

In step 318, the pore throat sizes are plotted as function of the relaxation times $T_2$ to obtain the surface relaxation.

In step 320, the pore size distribution of the reservoir is determined.

Figure 4A:
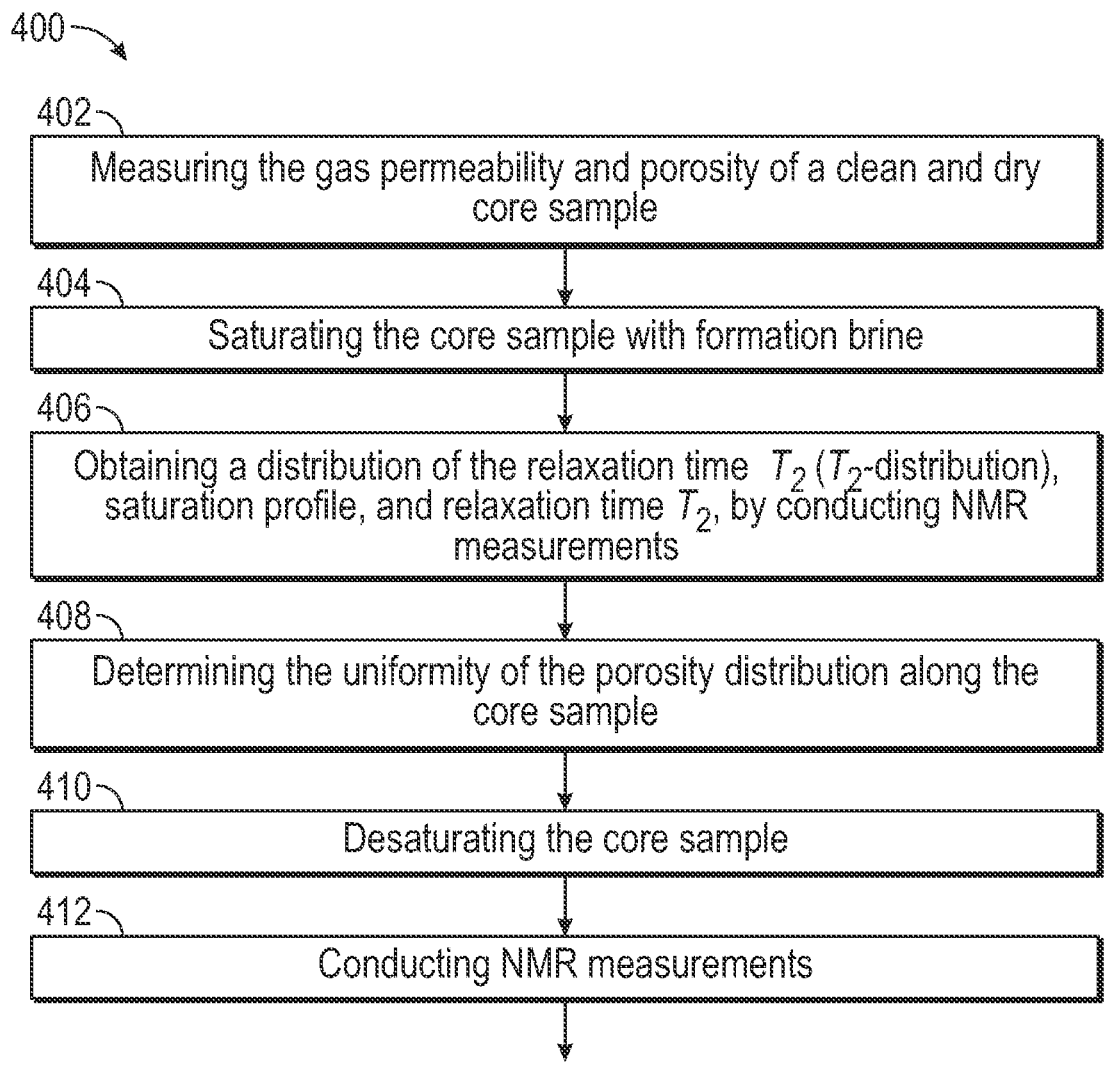
FIGS. 4A and 4B show a flowchart of the method steps for obtaining the intrinsic relaxation time in accordance with one or more embodiments disclosed herein.
Figure 4B:
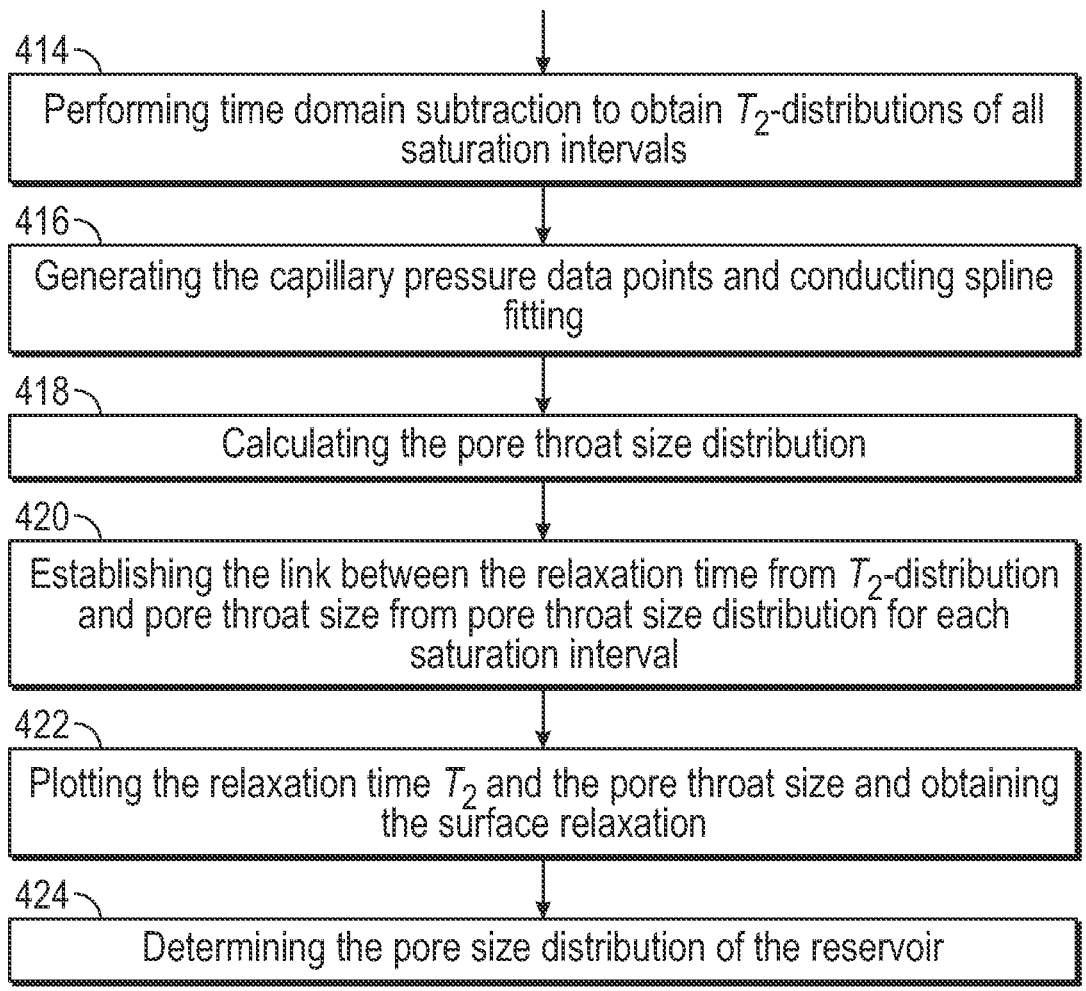

FIGS. 4A and 4B show a flowchart of the method steps 400 for obtaining the intrinsic relaxation. The method comprises the following steps.

In step 402, the gas permeability and porosity of a clean and dry core sample is measured. The core sample is cylindrical with a 1.5-inch diameter and 7 cm length is used.

In step 404, the core sample is saturated with formation brine. In one or more embodiments, formation brine is saturated with deionized water ($S_W$=100%).

In step 406, the distribution of the relaxation time $T_2$ ($T_2$-distribution), saturation profile, and relaxation time $T_2$ are obtained by conducting NMR measurements. The NMR measurement is non-destructive and is conveniently integrated into existing laboratory procedures.

In step 408, the uniformity of the porosity distribution along the core sample is determined. The heterogeneity affects the accuracy of the capillary pressure.

In step 410, the core sample is desaturated. The core sample is desaturated in a centrifuge starting from a low speed. The speed determination is by trial and error based on porosity and gas permeability. The desaturation of the core sample is gradually, such that the whole saturation range is covered. The desaturation of the core sample ends when either an irreducible saturation, or the maximum centrifuge speed is reached. The maximum speed depends on the sample integrity. Damage to the sample by large centrifugal force should be avoided.

In step 412, NMR measurements are conducted. The same NMR measurements comprise $T_2$ distribution, saturation profile, spatial and selective $T_2$ and are conducted based on the uniformity of the saturation profile.

Nuclear magnetic resonance (NMR) measures the rock property in the laboratory and in well logging for formation evaluation. NMR is non-destructive and easily performed and integrated into the experimental procedures. The transverse relaxation time $T_2$ distribution at 100% water saturation is associated with pore size distribution:

$$\frac{1}{T_2} = \frac{1}{T_{2bulk}} + \rho_2 \frac{S}{V} + \frac{(\gamma GTE)^2 D}{12} \approx \rho_2 \frac{S}{V} = \rho_2 \frac{3}{r_{body}}, \quad (1)$$

where $T_2$ is the transverse relaxation time, $\rho_2$ is the surface relaxation, S is the surface area of pore volume, V is the pore volume, $T_{2bulk}$ is the bulk water relaxation time, $\gamma$ is proton gyromagnetic ratio, G is the gradient strength, $T_3$ is the time of echo, and D is the diffusion coefficient.

The bulk and diffusion terms are often ignored in the laboratory, and this step assumes that the pore shape is spherical. The relaxation time $T_2$ is proportional to pore body size, and the proportionality coefficient is surface relaxation.

In one or more embodiments, magnetic resonance imaging (MRI) is performed, instead of NMR, to measure the $T_2$-distribution. MRI uses strong magnetic fields, magnetic field gradients, and radio waves to generate images. Exogenous contrast agents enhance the contrast of MRI. MRI is an application of NMR.

In step 414, time domain subtraction are performed to obtain $T_2$-distributions of all saturation levels.

In step 416, the capillary pressure data points are generated and spline fitting (smoothing splines) is conducted. Smoothing splines smooth noisy data.

In step 418, the pore throat size distribution is calculated.

NMR Pore Throat Size Distribution

The capillary pressure from NMR saturation profiles concerns the air/water. The saturation profiles are obtained from low centrifuge speeds to high centrifuge speeds. The capillary pressure is calculated directly from saturation and distance from the centrifugal center along the core length. A capillary pressure model according to Brooks, Corey, and Thomeer is generated by combining the saturation and capillary pressure data of all centrifuge speeds by data fitting. The pore throat size distribution is derived from the following equation obtained by capillary pressure models and raw capillary pressure and saturation data points:

$$f(r_{throat}) = \frac{dsS}{d(\log(r_{throat}))} \quad (2)$$

where S is the saturation, and r throat is obtained by using $$r_{throat} = \frac{2\sigma\cos\theta}{P_c}$$

from capillary pressure $P_c$ with $\theta$ as the contact angle, and $\sigma$ as the interfacial tension. However, the variation of complex pore size distribution is limited by the used capillary models. The pore size distribution is very scattering from raw capillary pressure saturation data due to heterogeneity along the core length.

In step 420, a link between the relaxation time from $T_2$-distribution and the pore throat size from pore throat size distribution is established for each saturation level.

In step 422, the relaxation time $T_2$ and the pore throat size is plotted and the surface relaxation is obtained. The surface relaxation is determined by a calibration procedure in which the specific surface area is measured on the same sample by other methods. The surface relaxation $T_2$ is determined by NMR measurements.

In step 424, the pore size distribution is determined. The surface relaxation is a vital parameter to convert the $T_2$-distribution of the NMR to pore size distribution. The pore size distribution is determined by the surface relaxivity, assuming a regular shape of the core sample (cylindrical or spherical). Surface relaxivity is directly obtained from pore size distribution from images and T2 distribution.

Pore Size Distributions

The observation of the microscopic pore space is achieved by imaging methods, such as thin section, SEM, and recent microCT derived from 2D and 3D images. The pore volume in sandstones is divided into large pores (body) connected by small pore throats for relatively simple inter-particle pore volumes.

The bulk volume of the core sample is measured by the mercury displacement method. First, a chamber is filled to a reference level and the volume is recorded. Then, the core sample is introduced and the new volume is recorded. The difference is the bulk volume of the sample. Mercury is used because it is strongly nonwetting.

The pore size distribution is determined by mercury injection capillary pressure (MICP). The entry of mercury into the pore volume is controlled by the pore throat, not by the pore body. The pore size distribution obtained by this method is the pore throat size and the accessible volume controlled by the throat size. The pore size distribution is different from the pore throat size distribution from the imaging methods. The simulation of mercury injection needs to be conducted on the pore network model or the microscopic pore space to obtain the pore size distribution by MICP. The size distribution in the pore body is obtained by the constant rate mercury injection capillary pressure, which is a variant of the MICP method.

As discussed in the above sections, the $T_2$-distributions indicate both pore body and pore throat sizes, but they mainly reflect pore body size distributions because of their large volume compared to pore throats. The pore throat size distributions by MICP or centrifuge methods indicate that the accessible volume fraction controls the size of a specific pore throat. Due to the irregular microscopic pores and their complex connectivity, one pore throat size controls a range of pore body size, and different pore throat sizes can control one pore body size. When two distributions were plotted together, the shapes and ranges do not match each other. The largest pore throat size from MICP should be less than the largest pore body size from $T_2$ distribution. The two distributions cannot be compared directly for pore size distribution analysis except for simple distributions of ideal porous media.

Another method to obtain surface relaxation is to compare the pore throat size distribution from MICP or other methods directly with the $T_2$-distribution. Note that relaxation is effective relaxation, including the body-throat size ratio. The method for determining the pore size distribution in a reservoir comprises obtaining intrinsic relaxation by NMR methods only.

$T_2$ Distribution Subtraction

Figure 5:
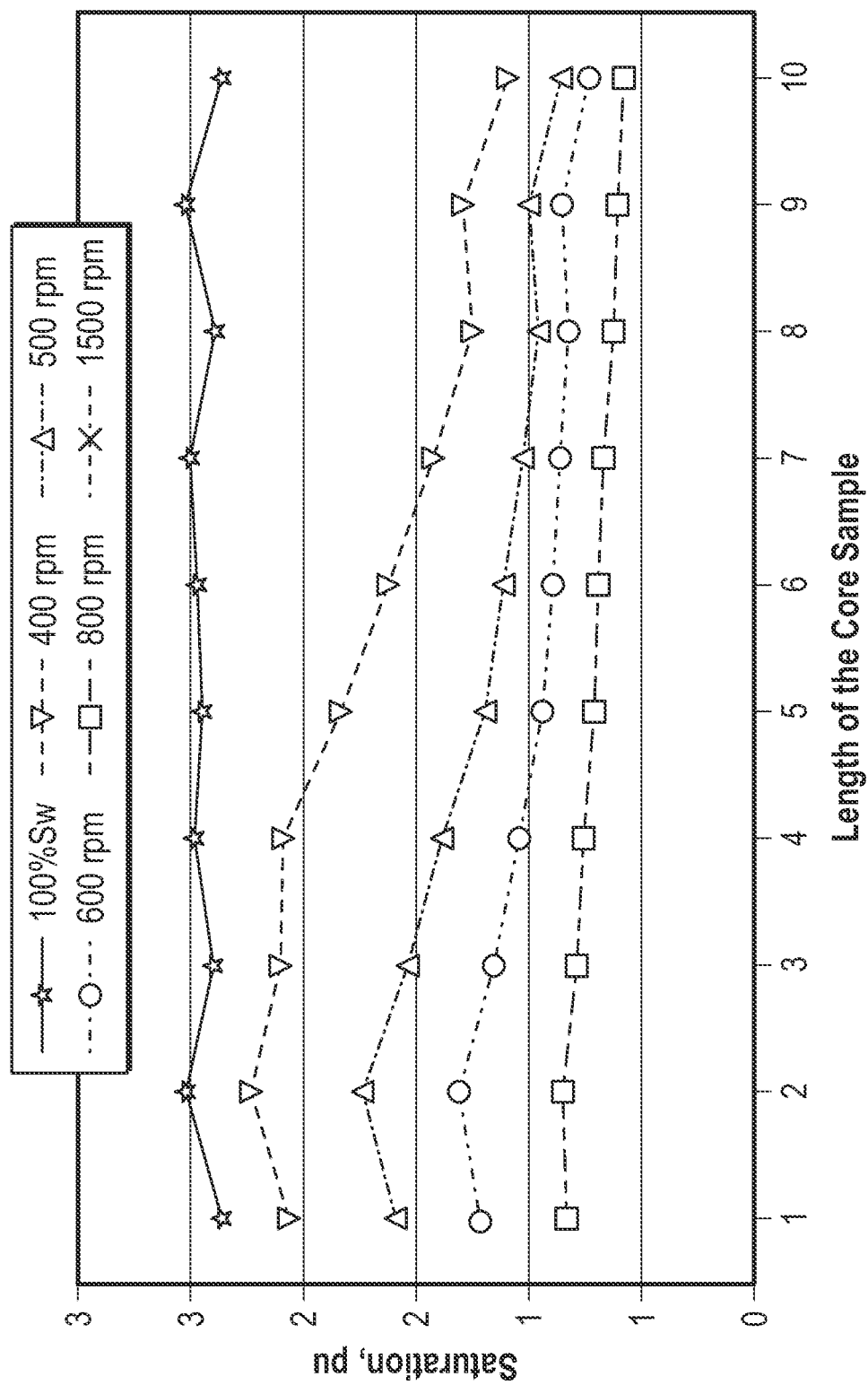
FIG. 5 shows saturation profiles of a core sample at different saturation levels in accordance with one or more embodiments disclosed herein.

FIG. 5 shows saturation profiles of a core sample at different saturation levels. The saturation levels start from full saturation ($S_W$=100%) to increasing centrifuge speeds (400 rpm, 500 rpm, 600 rpm, 800 rpm, 1500 rpm). The saturation level progressively decreases with increasing centrifuge speeds. As shown in the plot, the saturation profiles at 400 rpm and 500 rpm have large saturation gradients along the length of the core sample, while the saturation profiles at 800 rpm and 1500 rpm are relatively uniform.

Figure 6:
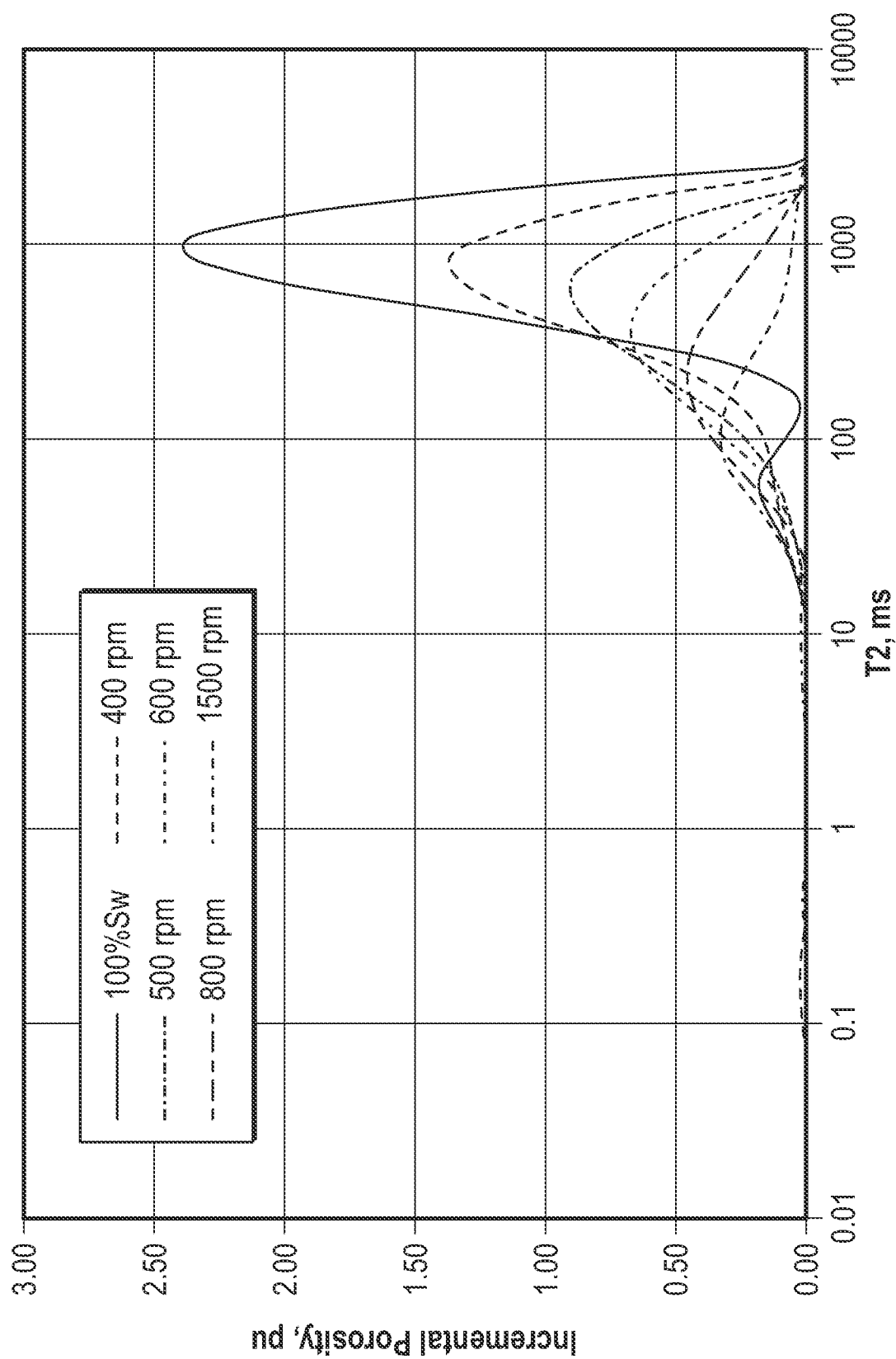
FIG. 6 shows $T_2$-distributions at different saturation levels in accordance with one or more embodiments disclosed herein.

FIG. 6 shows a plot of the porosity as function of the relaxation time $T_2$ ($T_2$-distribution) for different saturation levels. The $T_2$-distributions at different saturation levels are obtained from the average of similar slices along the length of the core sample from spatial $T_2$, or from the selective $T_2$ measurement based on the location of similar slices.

When the saturation level in the core sample reaches low levels at high centrifuge speeds, the saturation tends to be more uniform along the core sample. When there is a large saturation gradient, both spatial $T_2$ and selective $T_2$ are employed. For spatial $T_2$, the $T_2$-distributions of successive thin slices are measured along the length of the core sample. The $T_2$-distribution of a relatively uniform segment of the core sample is obtained by using wide slices or combining $T_2$-distribution of similar saturation levels. Selective $T_2$ is used to obtain a thick slice (~1 cm) of any segment of the core sample with a relatively uniform saturation level. The $T_2$-distributions at different saturation levels and their relaxation curves are obtained for further processing in this invention.

Figure 7:
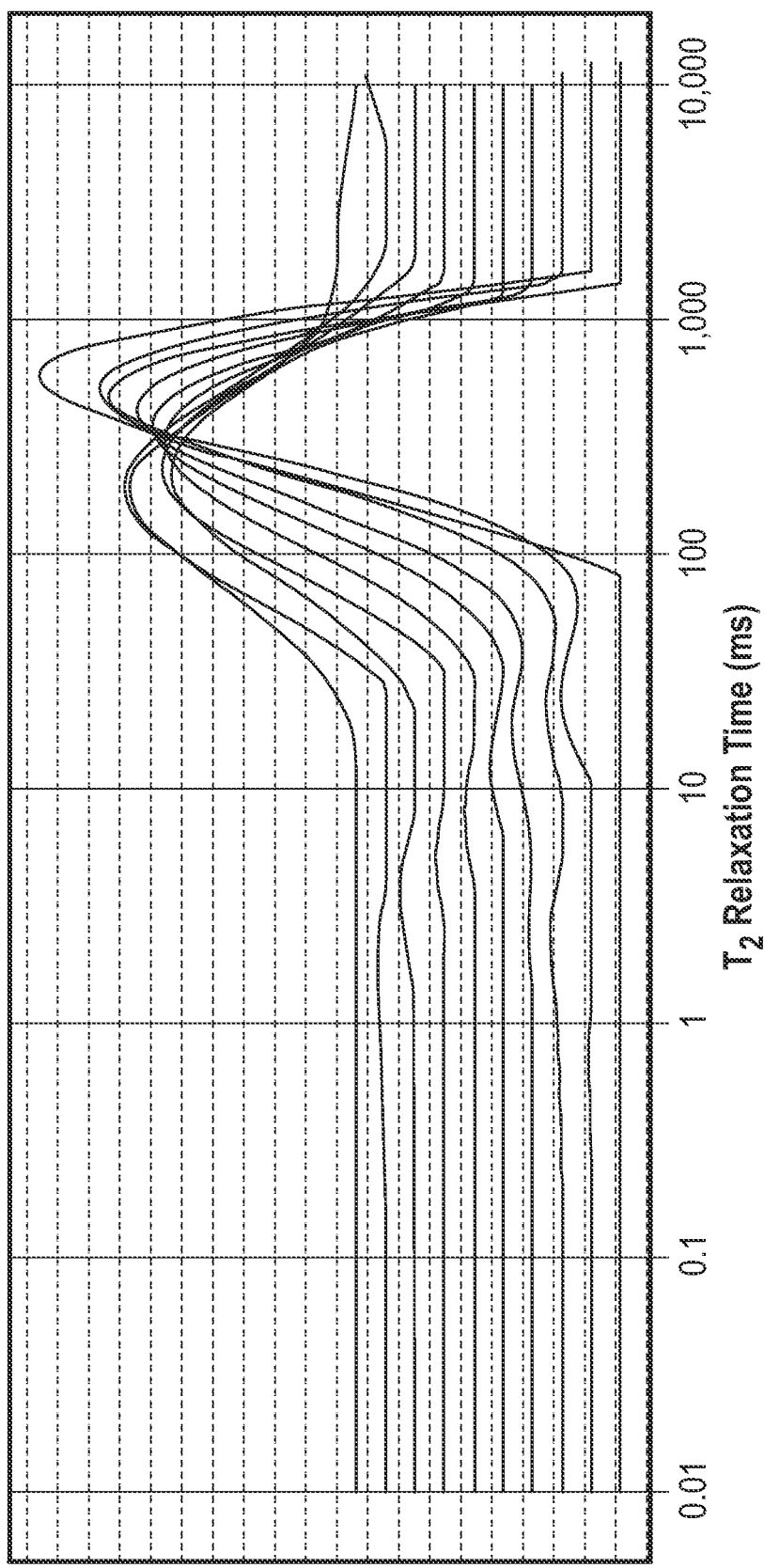
FIG. 7 shows spatial $T_2$-distributions in accordance with one or more embodiments disclosed herein.

FIG. 7 shows a plot of the relaxation times $T_2$ (spatial $T_2$-distributions) at 600 rpm. The y-axis shows the incremental saturation in porosity unit (p.u.). The $T_2$-distributions of desaturated water is obtained. Direct subtraction of $T_2$-distributions of less saturation levels from more saturation levels produce negative values. This is avoided by subtraction at the time domain. The subtraction is conducted on raw relaxations, and the resultant relaxation is inverted for the $T_2$ distribution.

Figure 8:
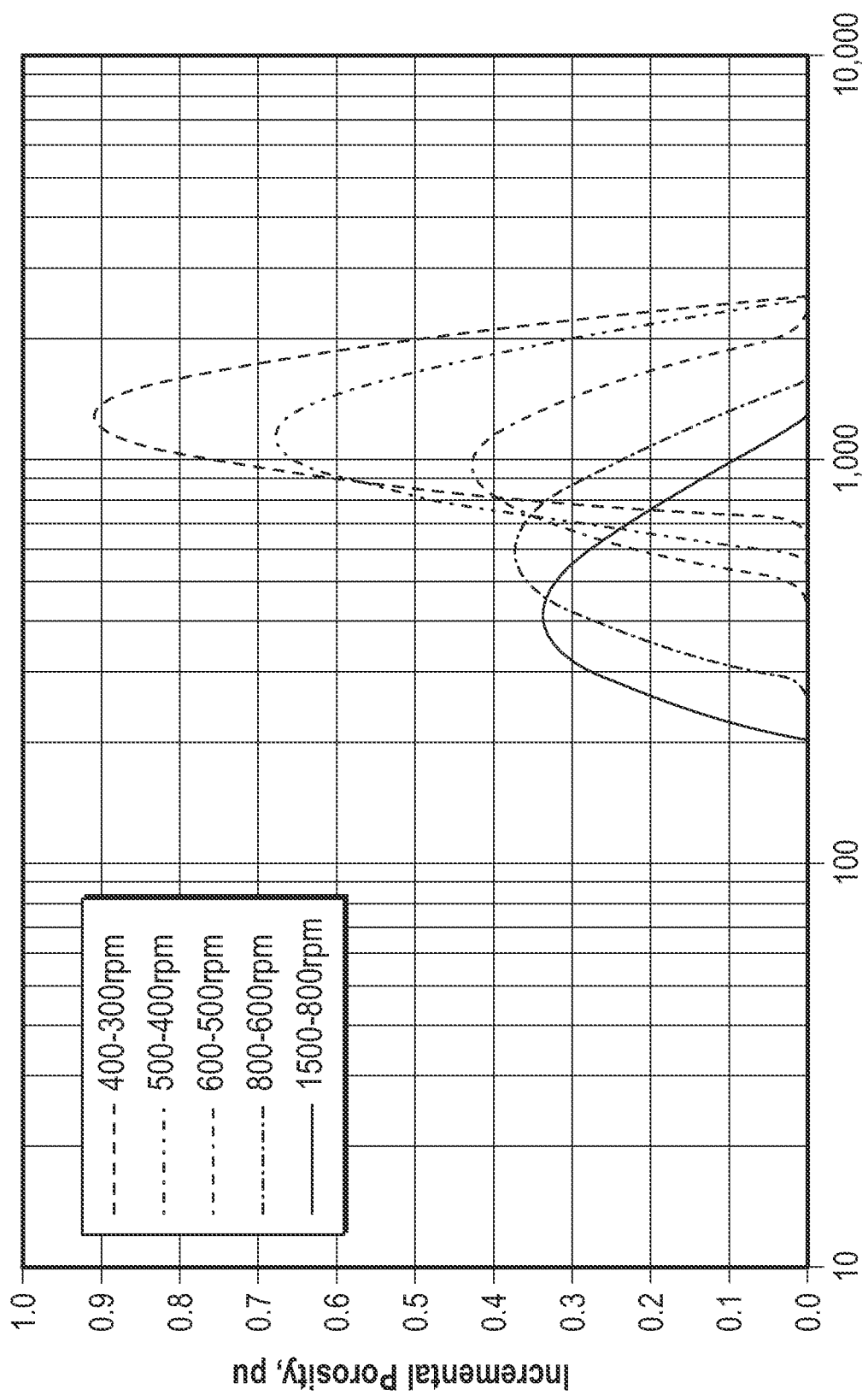
FIG. 8 shows the desaturated $T_2$-distributions from subtraction in accordance with one or more embodiments disclosed herein.

FIG. 8 shows a plot of the porosity as function of the relaxation time $T_2$ for five different saturation levels (1500-800 rpm, 800-600 rpm, 600-500 rpm, 500-400 rpm, and 400-300 rpm). The porosity is measured incrementally (not cumulative) and as a distribution of successive subtraction, which means that the subtraction is performed on every two speeds: between 300 and 400, 400 and 500, 500 and 600, 600 and 800, 800 and 1500 rpm.

As shown, each distribution corresponds to the pore and body size distribution controlled by a pore throat size range. The lower end of the distribution corresponds mostly to the pore throat, while the higher end of the distribution corresponds mainly pore body. The lower end corresponds to the low limit of pore throat size range. A connection is established to obtain the surface relaxation. The accuracy is improved by averaging over all desaturated distributions.

Figure 9:
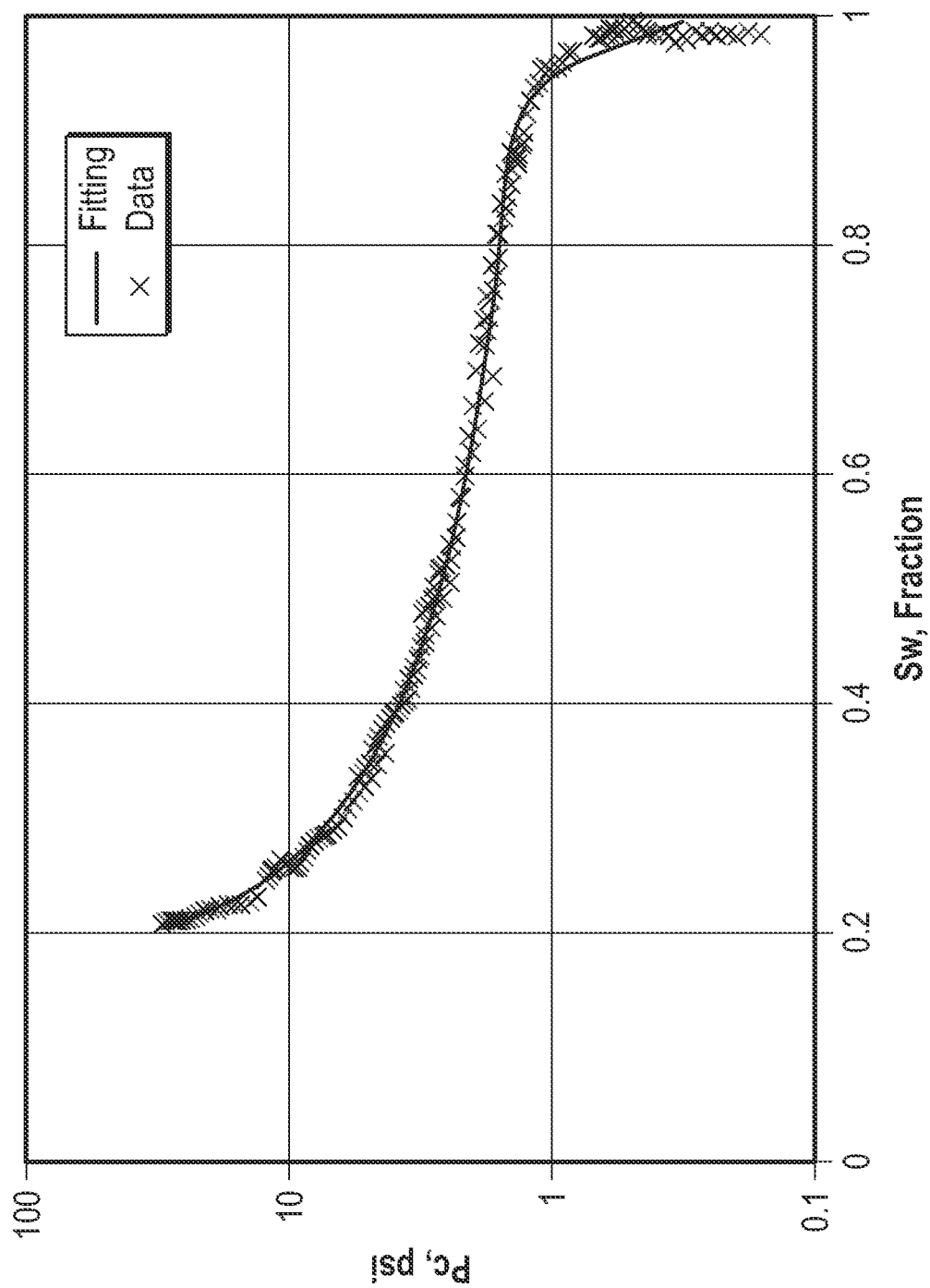
FIG. 9 shows a plot of the capillary pressure as a function of the saturation in the core sample in accordance with one or more embodiments disclosed herein.

FIG. 9 shows a plot of the capillary pressure $P_c$ (in psi) as a function of the saturation $S_W$ in the core sample. The plot shows that the fitting matches the measured data. The additional centrifuge speeds and profiles ensure that local variation is reflected by sufficient data points. The spline data fitting achieves the balance of the smoothness and the local variation.

Figure 10:
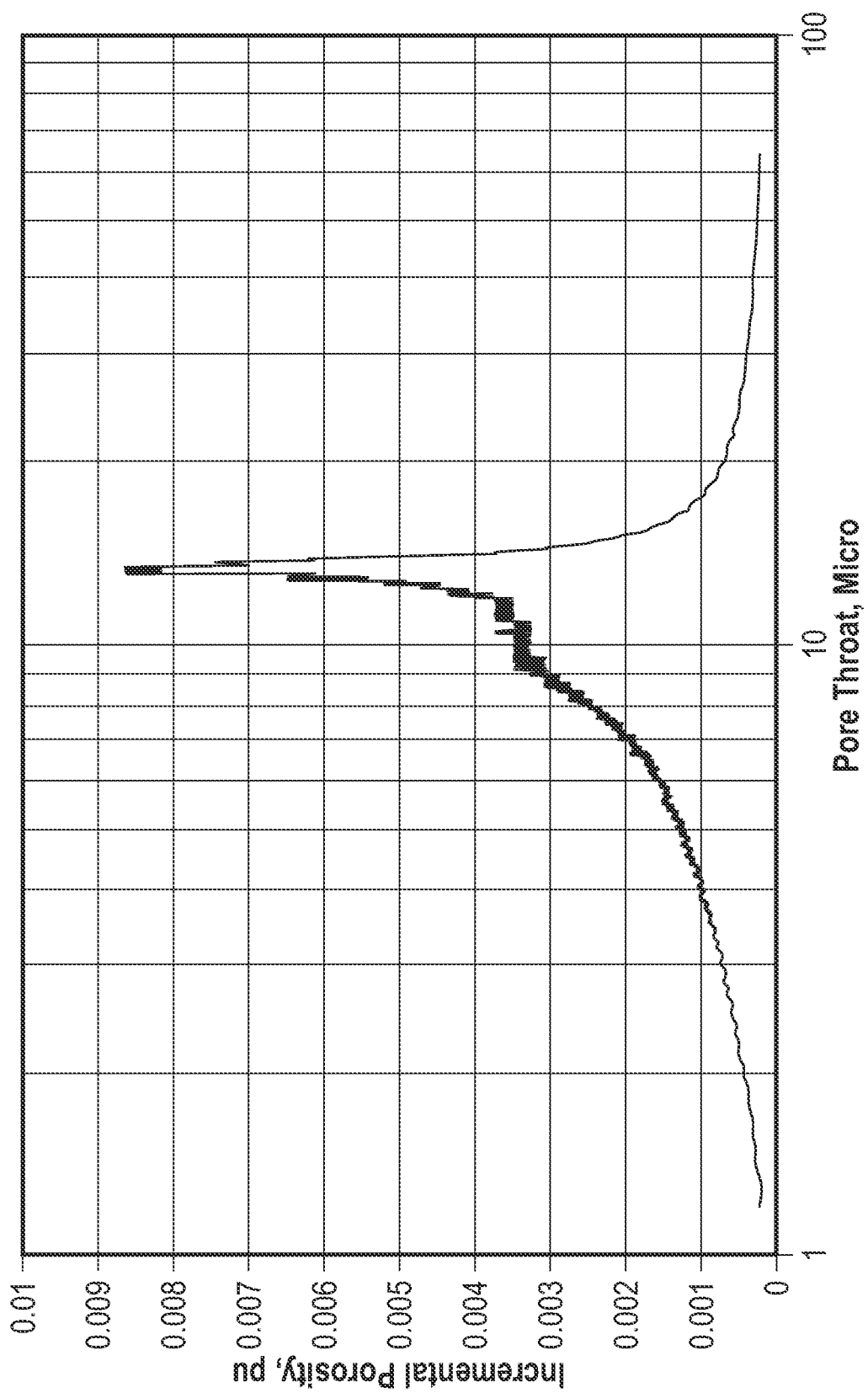
FIG. 10 shows the pore throat size distribution in accordance with one or more embodiments disclosed herein.

FIG. 10 shows a plot of the porosity as a function of the pore throat size in μm (pore throat size distribution). This plot is derived from FIG. 9 through the equation (2). The correspondence between desaturation curves in FIG. 8 and pore throat size distribution in FIG. 10 is established by saturation levels. For example, the $T_2$-distribution of 500-400 rpm is saturation level (0.3 to 0.48). The pore throat relaxation time is about 606 ms and the pore throat at saturation of 0.48 is 10.7 μm (see FIG. 8).

Figure 11:
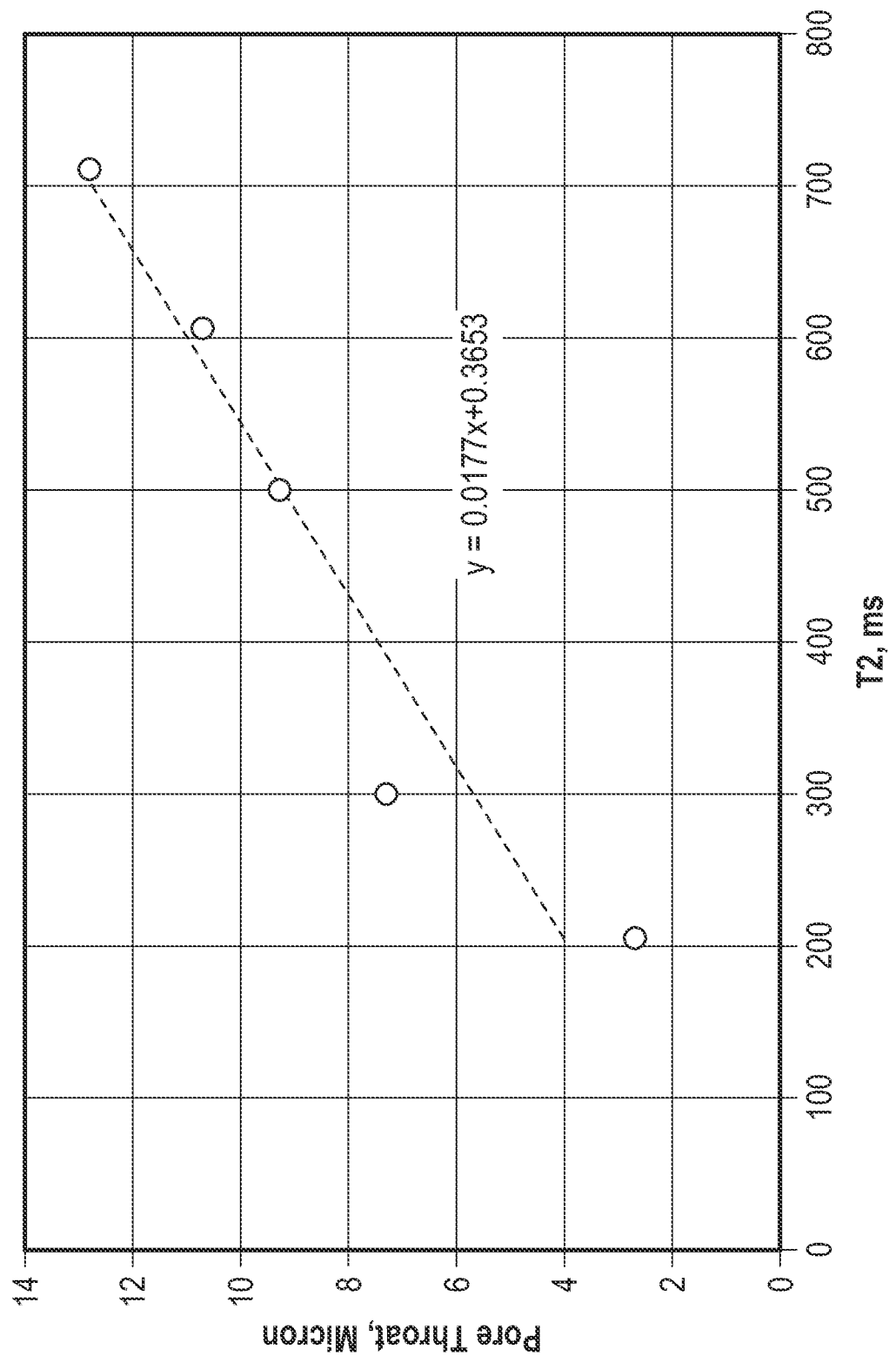
FIG. 11 shows the surface relaxation in accordance with one or more embodiments disclosed herein.

FIG. 11 shows a plot of the pore throat size in μm as function of the relaxation time $T_2$ in ms at different saturation levels (desaturation distribution). The average surface relaxation is 17.7 μm/s. Linear regression yields y=0.0177x+0.3653, where y is the pore throat size, and x is the relaxation time $T_2$.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for determining the pore size distribution in a reservoir, comprising the steps:
   drilling a core sample out of the reservoir,
   determining a porosity distribution along the core sample,
   obtaining $T_2$-distributions at different saturation levels of the core sample with formation brine,
   performing time domain subtraction on the $T_2$-distributions to obtain $T_2$-distributions at all saturation levels,
   determining pore throat size distribution along the core sample,
   determining first porosities from the $T_2$-distributions at all saturation levels that correspond to second porosities of the pore throat size distribution for each saturation level,
   determining $T_2$-distributions at the first porosities from the $T_2$-distributions,
   determining pore throat sizes at the second porosities from the pore throat size distributions,
   plotting the pore throat sizes as function of relaxation times $T_2$ to obtain surface relaxation, and
   determining the pore size distribution of the reservoir based on the obtained surface relaxation,
   wherein saturation profiles and/or $T_2$-distributions are obtained by nuclear magnetic resonance (NMR) measurements or by magnetic resonance imaging (MRI).

2. The method according to claim 1, wherein the formation brine is deionized water.

3. The method according to claim 1, wherein the core sample is rotated in a centrifuge to obtain the different saturation levels of the core sample.

4. The method according to claim 3, wherein the centrifuge starts from a low rotational speed.

5. The method according to claim 3, wherein the saturation level are estimated by porosity and gas permeability of the core sample to ensure that approximately ten saturation profiles are obtained at a saturation change of about 10%.

6. The method according to claim 3, wherein the rotational speed of the centrifuge is 400 rpm, 500 rpm, 600 rpm, 800 rpm, or 1500 rpm.

7. The method according to claim 1, wherein the relaxation time is a spatial relaxation time.

8. The method according to claim 1, wherein the relaxation time is a selective relaxation time $T_2$.

9. The method according to claim 1, wherein the core sample is clean and dry.

10. The method according to claim 1, further comprising generating capillary pressure data points and conducting spline fitting.

* * * * *